US012662463B2

(12) United States Patent
Xue et al.

(10) Patent No.: US 12,662,463 B2
(45) Date of Patent: Jun. 23, 2026

(54) METHOD FOR PREPARING ESOMEPRAZOLE MAGNESIUM TRIHYDRATE BY CRYSTAL TRANSFORMATION

(71) Applicant: SHANDONG ANALYSIS AND TEST CENTER, Jinan (CN)

(72) Inventors: Fumin Xue, Jinan (CN); Shuai Yu, Jinan (CN); Yuanchang Ma, Jinan (CN); Xujie Gao, Jinan (CN); Zihao Wang, Jinan (CN); Yaqi Han, Jinan (CN); Xingzhu Wang, Jinan (CN)

(73) Assignee: SHANDONG ANALYSIS AND TEST CENTER, Jinan (CN)

( * ) Notice: Subject to any disclaimer, the term of this patent is extended or adjusted under 35 U.S.C. 154(b) by 324 days.

(21) Appl. No.: 18/695,902

(22) PCT Filed: Oct. 18, 2023

(86) PCT No.: PCT/CN2023/125161
§ 371 (c)(1),
(2) Date: Mar. 27, 2024

(87) PCT Pub. No.: WO2024/156195
PCT Pub. Date: Aug. 2, 2024

(65) Prior Publication Data
US 2025/0115575 A1 Apr. 10, 2025

(30) Foreign Application Priority Data
Jan. 29, 2023 (CN) .......................... 202310076656.0

(51) Int. Cl.
*C07D 401/12* (2006.01)
(52) U.S. Cl.
CPC .................................. *C07D 401/12* (2013.01)
(58) Field of Classification Search
CPC .......................... C07D 401/12; C07B 2200/13
See application file for complete search history.

(56) References Cited

U.S. PATENT DOCUMENTS

| | | | |
|---|---|---|---|
| 6,747,155 B2 * | 6/2004 | Kronstrom | C07D 401/12 |
| | | | 546/273.7 |
| 2003/0004190 A1 | 1/2003 | Kronstrom et al. | |
| 2021/0313015 A1 * | 10/2021 | Sukegawa | C30B 29/58 |

FOREIGN PATENT DOCUMENTS

| | | |
|---|---|---|
| CN | 103664888 A | 3/2014 |
| CN | 104356114 A | 2/2015 |
| CN | 111072633 A | 4/2020 |
| CN | 113278008 A | 8/2021 |
| CN | 113387929 A | 9/2021 |
| CN | 116102538 A | 5/2023 |
| WO | 2007/031845 A2 | 3/2007 |

OTHER PUBLICATIONS

Gao et al., "Crystal form control of the reactive crystallization process of esomeprazole magnesium trihydrate", Shandong Science, vol. 35, No. 3, Jun. 30, 2022, pp. 138-144.

* cited by examiner

*Primary Examiner* — Jeffrey S Lundgren
*Assistant Examiner* — W. Justin Youngblood
(74) *Attorney, Agent, or Firm* — Oliff PLC

(57) ABSTRACT

The invention discloses a method for preparing esomeprazole magnesium trihydrate by crystal transformation, and relates to the technical field of pharmaceutical preparations and crystallization. It includes the following steps of preparing an esomeprazole potassium aqueous solution, preparing a magnesium sulfate heptahydrate aqueous solution, a reactive crystallization process to obtain the esomeprazole magnesium tetrahydrate, and filtering the obtained esomeprazole magnesium tetrahydrate to obtain a sphaerocrystal of esomeprazole magnesium trihydrate. The method for preparing esomeprazole magnesium trihydrate by crystal transformation in the present invention is characterized by using the esomeprazole potassium aqueous solution and the magnesium sulfate aqueous solution for ion exchange to obtain the esomeprazole magnesium tetrahydrate. The whole process takes only about 1 hour, which greatly shortens the reaction time, and the obtained esomeprazole magnesium trihydrate has high purity, large particle size, narrow distribution, small angle of repose and good fluidity.

5 Claims, 5 Drawing Sheets

METHOD FOR PREPARING ESOMEPRAZOLE MAGNESIUM TRIHYDRATE BY CRYSTAL TRANSFORMATION

FIELD

The present invention refers to the technical field of pharmaceutical preparations and crystallization, in particular to a method for preparing esomeprazole magnesium trihydrate by crystal transformation.

BACKGROUND

Esomeprazole magnesium trihydrate, chemically known as bis-(S)-5-methoxy-2-[[(4-methoxy-3, 5-dimethyl-2-pyridyl)methyl] sulfenyl]-1H-benzimidazole magnesium, is the S isomer hydrate of omeprazole, and it is used in the treatment of erosive reflux esophagus inflammation, long-term maintenance therapy to prevent recurrence in the cured patients with esophagitis, symptom control of gastroesophageal reflux disease, etc., with good treatment effect. Esomeprazole magnesium trihydrate is the most effective and best-selling drug in esomeprazole magnesium series, including esomeprazole magnesium and esomeprazole magnesium dihydrate, etc.

At present, the crystallization process of esomeprazole magnesium trihydrate has some problems such as long operation cycle, and the complicated reactive crystallization steps will greatly prolong the operation time, so as to affect the production speed. If only the reactive crystallization speed is pursued, there will be problems such as poor crystallinity and stability, wide distribution of particle size, etc.

In addition, esomeprazole magnesium trihydrate needs to be separated from water or aqueous systems. In the process of preparing esomeprazole magnesium trihydrate particles, there is still a problem of high viscosity of wet products, and the moisture content of wet products can reach 80%, which needs to be dried. However, the trihydrate is unstable at high temperature. If the conventional flat oven is used, 7~8 days of the drying cycle will be need, which is long, and the final esomeprazole magnesium trihydrate product looks yellow, with the purity reduced.

SUMMARY

In order to solve the problems of long preparation time, poor drying method, poor appearance and low purity of the esomeprazole magnesium trihydrate, the purpose of the present invention is to provide a method for preparing esomeprazole magnesium trihydrate by crystal transformation.

The purpose of the present invention is realized by the following technical solution:

A method for preparing esomeprazole magnesium trihydrate by crystal transformation, comprising the following steps:

① preparation of esomeprazole potassium aqueous solution: according to part by weight, adding 35~45 parts of esomeprazole potassium into 500~1000 parts of the first deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 15~20 parts of magnesium sulfate heptahydrate into 280~420 parts of the second deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 15~20° C., starting to stir, adding the magnesium sulfate heptahydrate aqueous solution obtained in Step ② and with the mass of ¹/₁₀~¹/₈ into the crystallization kettle, stirring them for 10~15 minutes, and then adding the remained magnesium sulfate heptahydrate aqueous solution obtained in Step ② into the crystallization kettle within 30 minutes, and stirring at 15-20° C. for crystallization for 30~40 minutes to obtain the esomeprazole magnesium tetrahydrate; and ④ filtering the esomeprazole magnesium tetrahydrate obtained in Step ③, washing the filter cake in the deionized water, putting the filter cake into a vacuum drier, and drying at 35~45° C. for 5~6 hours to obtain a sphaerocrystal of esomeprazole magnesium trihydrate.

Preferably, Step ① is as follows: adding 40 parts of esomeprazole potassium into 600 parts of the first deionized water.

Preferably, Step ② is as follows: adding 17 parts of magnesium sulfate heptahydrate into 300 parts of the second deionized water.

Preferably, the temperature of the crystallization kettle is 18° C.

Preferably, a water soluble dispersant is added into the crystallization kettle after the magnesium sulfate heptahydrate aqueous solution is added, wherein the mass of the water soluble dispersant is 1~5% of the mass of the esomeprazole potassium in Step ①, and the water soluble dispersant is isomeric alcohol ethoxylates or sodium ligninsulfonate.

Compared with the prior art, the present invention has the advantages as follows:

The method for preparing esomeprazole magnesium trihydrate by crystal transformation in the present invention is characterized by using the esomeprazole potassium aqueous solution and the magnesium sulfate aqueous solution for ion exchange to obtain the esomeprazole magnesium tetrahydrate. The whole process takes only about 1 hour, which greatly shortens the reaction time, and the obtained esomeprazole magnesium trihydrate has high purity, large particle size, narrow distribution, small angle of repose and good fluidity.

DESCRIPTION OF THE DRAWINGS

The scale in the lower right corner of FIG. 1 and FIG. 5 is 50 um.

DETAILED DESCRIPTION OF THE EMBODIMENTS

Figure 1:
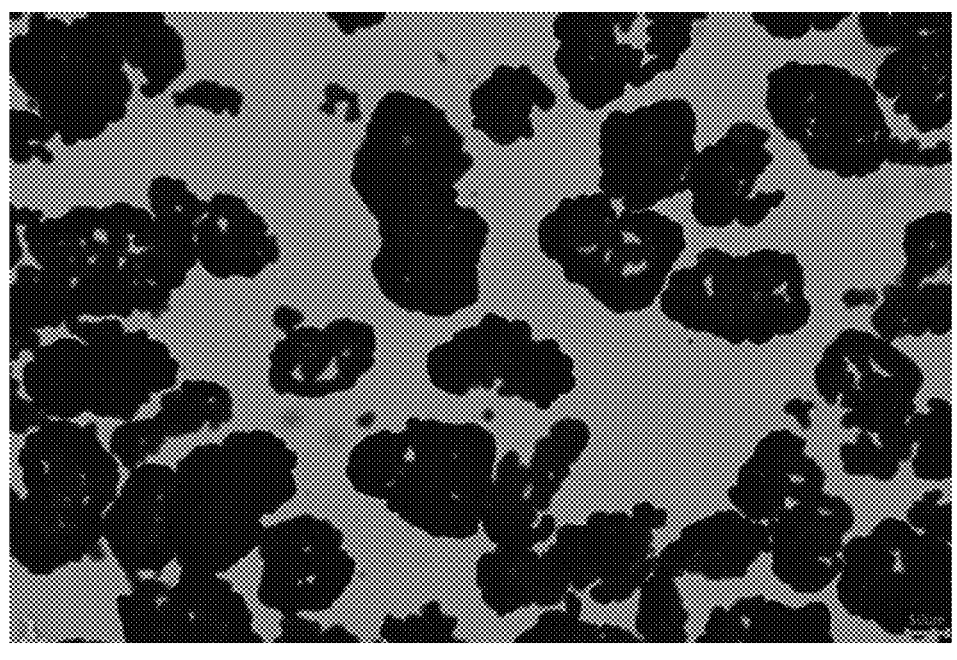
FIG. 1 shows a micrograph of esomeprazole magnesium tetrahydrate.

The purpose of the present invention is to provide a method for preparing esomeprazole magnesium trihydrate by crystal transformation, which is realized by the following technical solution:

A method for preparing esomeprazole magnesium trihydrate by crystal transformation, comprising the following steps:

① preparation of esomeprazole potassium aqueous solution: according to part by weight, adding 35~45 parts of esomeprazole potassium into 500~1000 parts of the first deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 15~20 parts of magnesium sulfate heptahydrate into 280~420 parts of the second deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 15~20° C., starting to stir, adding the magnesium sulfate heptahydrate aqueous solution obtained in Step ② and with the mass of ¹⁄₁₀~¹⁄₈ into the crystallization kettle, stirring them for 10~15 minutes, and then adding the remained magnesium sulfate heptahydrate aqueous solution obtained in Step ② into the crystallization kettle within 30 minutes, and stirring at 15-20° C. for crystallization for 30~40 minutes to obtain the esomeprazole magnesium tetrahydrate; and ④ filtering the esomeprazole magnesium tetrahydrate obtained in Step ③, washing the filter cake in the deionized water, putting the filter cake into a vacuum drier, and drying at 35~45° C. for 5~6 hours to obtain a sphaerocrystal of esomeprazole magnesium trihydrate.

Preferably, Step ① is as follows: adding 40 parts of esomeprazole potassium into 600 parts of the first deionized water.

Preferably, Step ② is as follows: adding 17 parts of magnesium sulfate heptahydrate into 300 parts of the second deionized water.

Preferably, the temperature of the crystallization kettle is 18° C.

Preferably, a water soluble dispersant is added into the crystallization kettle after the magnesium sulfate heptahydrate aqueous solution is added, wherein the mass of the water soluble dispersant is 1~5% of the mass of the esomeprazole potassium in Step ①, and the water soluble dispersant is isomeric alcohol ethoxylates or sodium ligninsulfonate.

The present invention is further described in combination with the specific embodiments.

Embodiment 1

A method for preparing esomeprazole magnesium trihydrate by crystal transformation, comprising the following steps:

① preparation of esomeprazole potassium aqueous solution: adding 350 g of esomeprazole potassium into 5 kg of the deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 150 g of magnesium sulfate heptahydrate into 2.8 kg of the deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 15° C., starting to stir, adding 295 g of magnesium sulfate heptahydrate aqueous solution obtained in Step ② into the crystallization kettle, stirring them for 10 min, and then adding the remained magnesium sulfate heptahydrate aqueous solution obtained in Step ② into the crystallization kettle within 20 minutes, and stirring at 15° C. for crystallization for 30 minutes to obtain the esomeprazole magnesium tetrahydrate; and ④ filtering the esomeprazole magnesium tetrahydrate obtained in Step ③, washing the filter cake in the deionized water, putting the filter cake into a vacuum drier, and drying at 35° C. for 5 hours to obtain a sphaerocrystal of esomeprazole magnesium trihydrate.

Embodiment 2

A method for preparing esomeprazole magnesium trihydrate by crystal transformation, comprising the following steps:

① preparation of esomeprazole potassium aqueous solution: adding 450 g of esomeprazole potassium into 10 kg of the first deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 200 g of magnesium sulfate heptahydrate into 4.2 kg of the second deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 20° C., starting to stir, adding 550 g of magnesium sulfate heptahydrate aqueous solution obtained in Step ② into the crystallization kettle, stirring them for 15 min, and then adding the remained magnesium sulfate heptahydrate aqueous solution obtained in Step ② into the crystallization kettle within 30 minutes, and stirring at 20° C. for crystallization for 40 minutes to obtain the esomeprazole magnesium tetrahydrate; and ④ filtering the esomeprazole magnesium tetrahydrate obtained in Step (3), washing the filter cake in the deionized water, putting the filter cake into a vacuum drier, and drying at 45° C. for 6 hours to obtain a sphaerocrystal of esomeprazole magnesium trihydrate.

Embodiment 3

A method for preparing esomeprazole magnesium trihydrate by crystal transformation, comprising the following steps:

① preparation of esomeprazole potassium aqueous solution: adding 380 g of esomeprazole potassium into 6 kg of the deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 180 g of magnesium sulfate heptahydrate into 3 kg of the deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 16° C., starting to stir, adding 350 g of magnesium sulfate heptahydrate aqueous solution obtained in Step ② into the crystallization kettle, stirring them for 12 min, and then adding the remained magnesium sulfate heptahydrate aqueous solution obtained in Step ② into the crystallization kettle within 30 minutes, and stirring at 16° C. for crystallization for 32 minutes to obtain the esomeprazole magnesium tetrahydrate; and ④ filtering the esomeprazole magnesium tetrahydrate obtained in Step (3), washing the filter cake in the deionized water, putting the filter cake into a vacuum drier, and drying at 38° C. for 5.5 hours to obtain a sphaerocrystal of esomeprazole magnesium trihydrate.

Embodiment 4

A method for preparing esomeprazole magnesium trihydrate by crystal transformation, comprising the following steps:

① preparation of esomeprazole potassium aqueous solution: adding 420 g of esomeprazole potassium into 6.5 kg of the deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 160 g of magnesium sulfate heptahydrate into 3.5 kg of the deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 18° C., starting to stir, adding 400 g of magnesium sulfate heptahydrate aqueous solution obtained in Step ② into the crystallization kettle, stirring them for 14 minutes, and then adding the remained magnesium sulfate heptahydrate aqueous solution obtained in Step ② into the crystallization kettle within 25 minutes, and stirring at 18° C. for crystallization for 38 minutes to obtain the esomeprazole magnesium tetrahydrate; and ④ filtering the esomeprazole magnesium tetrahydrate obtained in Step (3), washing the filter cake in the deionized water, putting the filter cake into a vacuum drier, and drying at 42° C. for 5 hours to obtain a sphaerocrystal of esomeprazole magnesium trihydrate.

Embodiment 5

A method for preparing esomeprazole magnesium trihydrate by crystal transformation, comprising the following steps:

① preparation of esomeprazole potassium aqueous solution: adding 400 g of esomeprazole potassium into 6 kg of the deionized water, stirring and dissolving them, and filtering the mixture with 0.45 microns of aqueous phase filter membrane to obtain the esomeprazole potassium aqueous solution;

② preparation of magnesium sulfate heptahydrate aqueous solution: adding 170 g of magnesium sulfate heptahydrate into 3 kg of the deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 18° C., starting to stir, adding 350 g of magnesium sulfate heptahydrate aqueous solution obtained in Step ② into the crystallization kettle, stirring them for 12 minutes, and then adding the remained magnesium sulfate heptahydrate aqueous solution obtained in Step ② into the crystallization kettle within 30 minutes, and stirring at 18° C. for crystallization for 35 minutes to obtain the esomeprazole magnesium tetrahydrate; and ④ filtering the esomeprazole magnesium tetrahydrate obtained in Step (3), washing the filter cake in the deionized water, putting the filter cake into a vacuum drier, and drying at 40° C. for 5 hours to obtain a sphaerocrystal of esomeprazole magnesium trihydrate.

Embodiment 6

A method for preparing esomeprazole magnesium trihydrate by crystal transformation is the same as the steps in Embodiment 3. The difference is that 3.8 g of isomeric alcohol ethoxylates is added into the crystallization kettle after the magnesium sulfate heptahydrate aqueous solution is added in Step 3.

Embodiment 7

A method for preparing esomeprazole magnesium trihydrate by crystal transformation is the same as the steps in Embodiment 4. The difference is that 21 g of isomeric alcohol ethoxylates is added into the crystallization kettle after the magnesium sulfate heptahydrate aqueous solution is added in Step (3).

Embodiment 8

A method for preparing esomeprazole magnesium trihydrate by crystal transformation is the same as the steps in Embodiment 5. The difference is that 10 g of isomeric alcohol ethoxylates is added into the crystallization kettle after the magnesium sulfate heptahydrate aqueous solution is added in Step 3.

Embodiment 9

A method for preparing esomeprazole magnesium trihydrate by crystal transformation is the same as the steps in Embodiment 3. The difference is that 3.8 g of sodium ligninsulfonate is added into the crystallization kettle after the magnesium sulfate heptahydrate aqueous solution is added in Step 3.

Embodiment 10

A method for preparing esomeprazole magnesium trihydrate by crystal transformation is the same as the steps in Embodiment 4. The difference is that 21 g of sodium ligninsulfonate is added into the crystallization kettle after the magnesium sulfate heptahydrate aqueous solution is added in Step ③.

Embodiment 11

A method for preparing esomeprazole magnesium trihydrate by crystal transformation is the same as the steps in Embodiment 5. The difference is that 10 g of sodium ligninsulfonate is added into the crystallization kettle after the magnesium sulfate heptahydrate aqueous solution is added in Step ③.

Through test for the mean particle size, distribution span of particle size, and angle of repose of the esomeprazole magnesium trihydrate obtained in Embodiments 1~11 and the purchased esomeprazole magnesium trihydrate, the results are as shown in Table 1.

TABLE 1

| Results of Particle Size and Angle of Repose | | | |
|---|---|---|---|
| | | Distribution span | |
| | Mean particle | of particle size | Angle of |
| Purity (%) | size (μm) | $(D_{90}-D_{10})/D_{50}$ | repose/° |
| Embodiment 1 99.91 | 125 | 1.05 | 25 |
| Embodiment 2 99.90 | 136 | 1.11 | 27 |
| Embodiment 3 99.92 | 130 | 1.06 | 26 |
| Embodiment 4 99.94 | 132 | 1.06 | 24 |
| Embodiment 5 99.93 | 128 | 1.08 | 23 |
| Embodiment 6 99.91 | 140 | 1.05 | 25 |
| Embodiment 7 99.92 | 145 | 1.04 | 23 |
| Embodiment 8 99.91 | 136 | 1.06 | 24 |
| Embodiment 9 99.92 | 141 | 1.05 | 24 |
| Embodiment 10 99.93 | 144 | 1.06 | 25 |
| Embodiment 11 99.91 | 135 | 1.07 | 26 |
| Purchased 98.56 esomeprazole magnesium trihydrate | 65 | 2.12 | 35 |

It can be seen from the results in Table 1 that the esomeprazole magnesium trihydrate obtained by the present invention has high purity and large particle size, especially after the addition of dispersant, the particle size is further increased, because the dispersibility of esomeprazole magnesium trihydrate is better after the water soluble dispersant is added, and small particles are more likely to aggregate into large particles; the purity of the esomeprazole magnesium trihydrate will not be affected by taking isomeric alcohol ethoxylates or sodium ligninsulfonate as the water soluble dispersant. However, the existing purchased esomeprazole magnesium trihydrate has low purity, small particle size, uneven appearance of particles, with agglomeration phenomenon, large distribution span of particle size, and poor dispersion.

Compared with the existing products, the esomeprazole magnesium trihydrate obtained by the present invention has a small increase in purity, and the main difference is that the fluidity is improved. The influence of particle size and angle of repose on the tablet is mainly reflected in the fluidity of the sample. If the particles of the drug are relatively concentrated in the distribution of particle size, the discrete state will be small and the angle of repose will be low, so that the particles will have good fluidity, and will be more uniform in the tablet pressing process, so as to reduce the difference in the weight of the tablet. However, if the distribution of particle size of the drug particles is relatively dispersed, the angle of repose of the particles is large, and the particle fluidity is low, the particles will be unevenly filled in the tablet pressing process.

Figure 2:
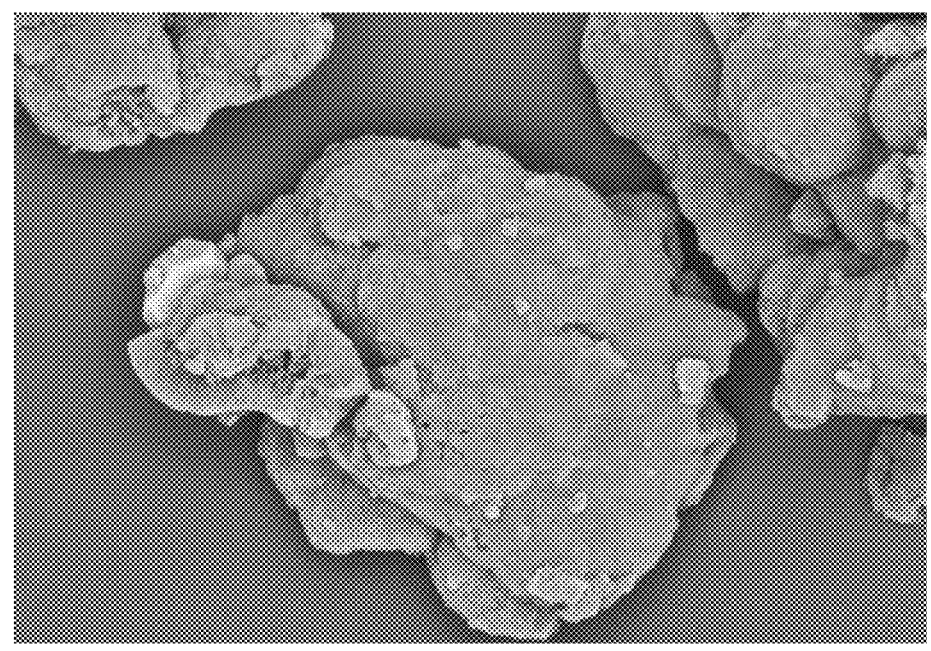
FIG. 2 shows a SEM graph of esomeprazole magnesium tetrahydrate.
Figure 3:
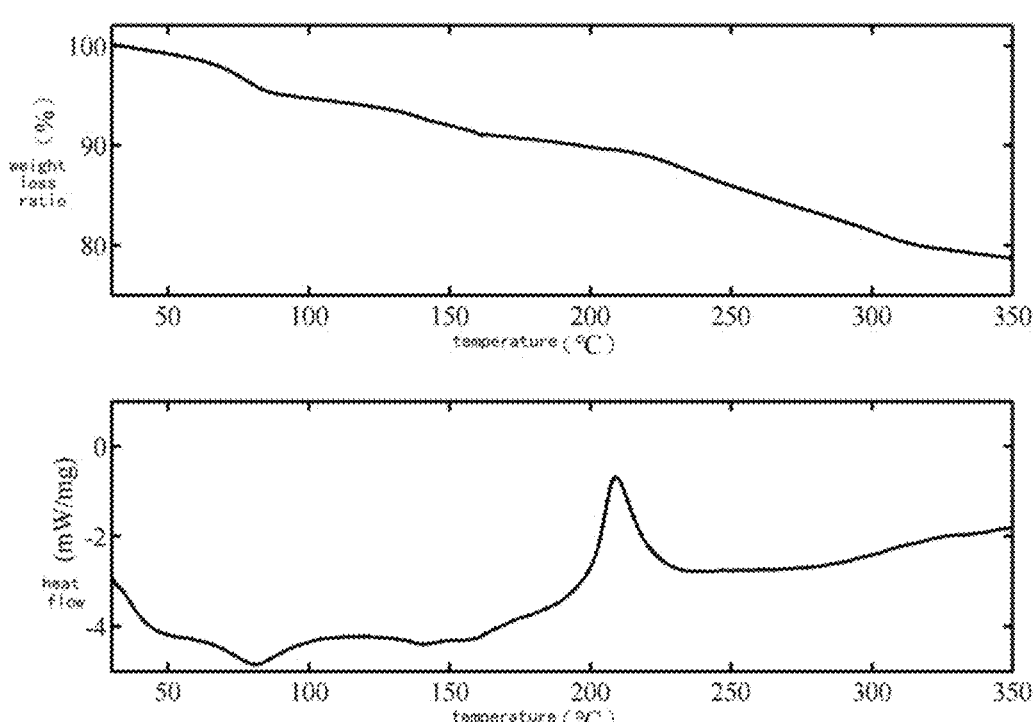
FIG. 3 shows a thermogram of esomeprazole magnesium tetrahydrate.
Figure 4:
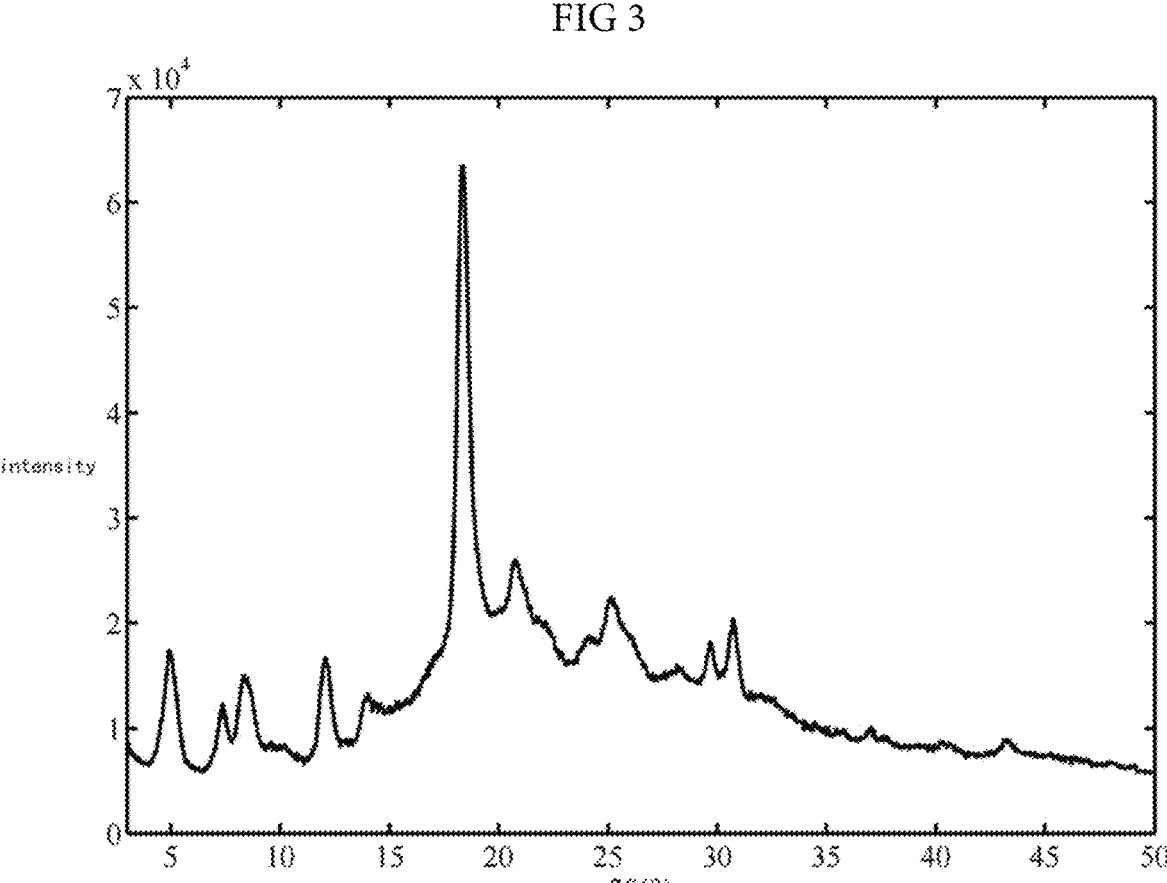
FIG. 4 shows an XRD spectrum of esomeprazole magnesium tetrahydrate.
Figure 5:
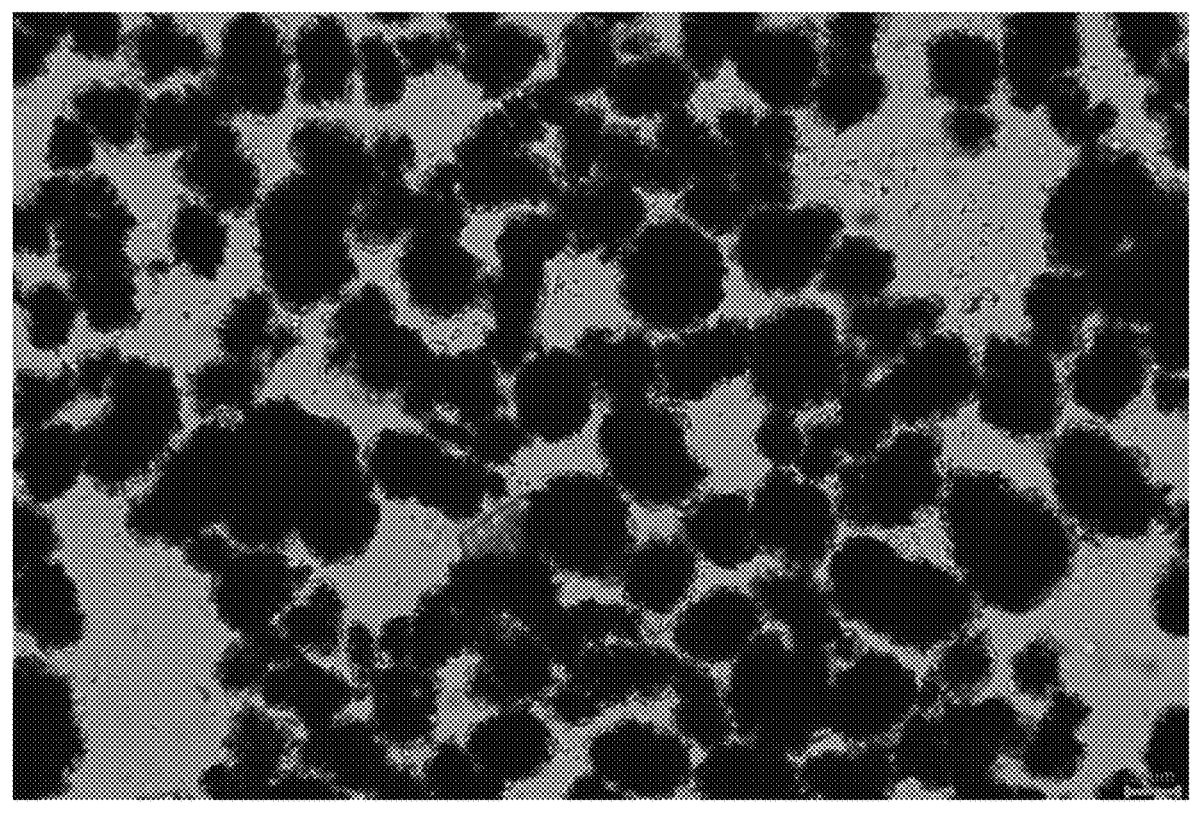
FIG. 5 shows a micrograph of esomeprazole magnesium trihydrate.
Figure 6:
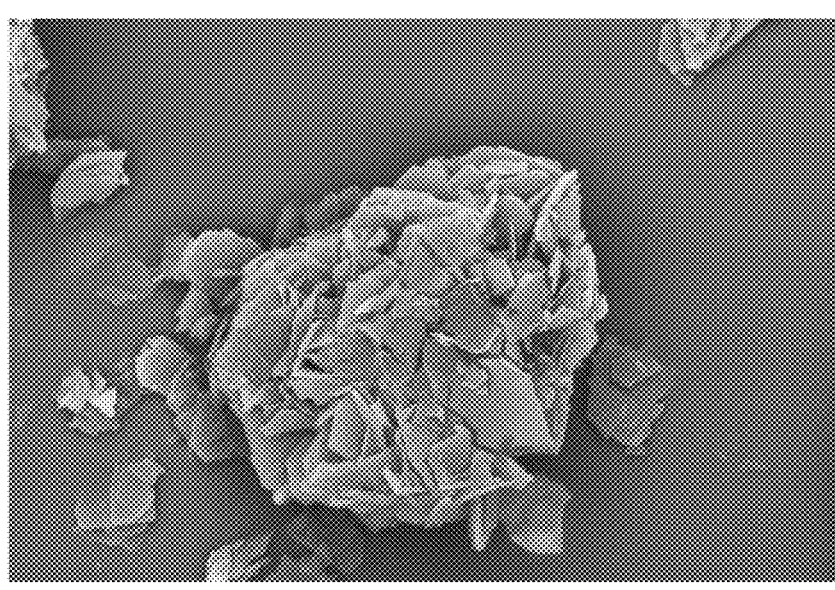
FIG. 6 shows a SEM graph of esomeprazole magnesium trihydrate.
Figure 7:
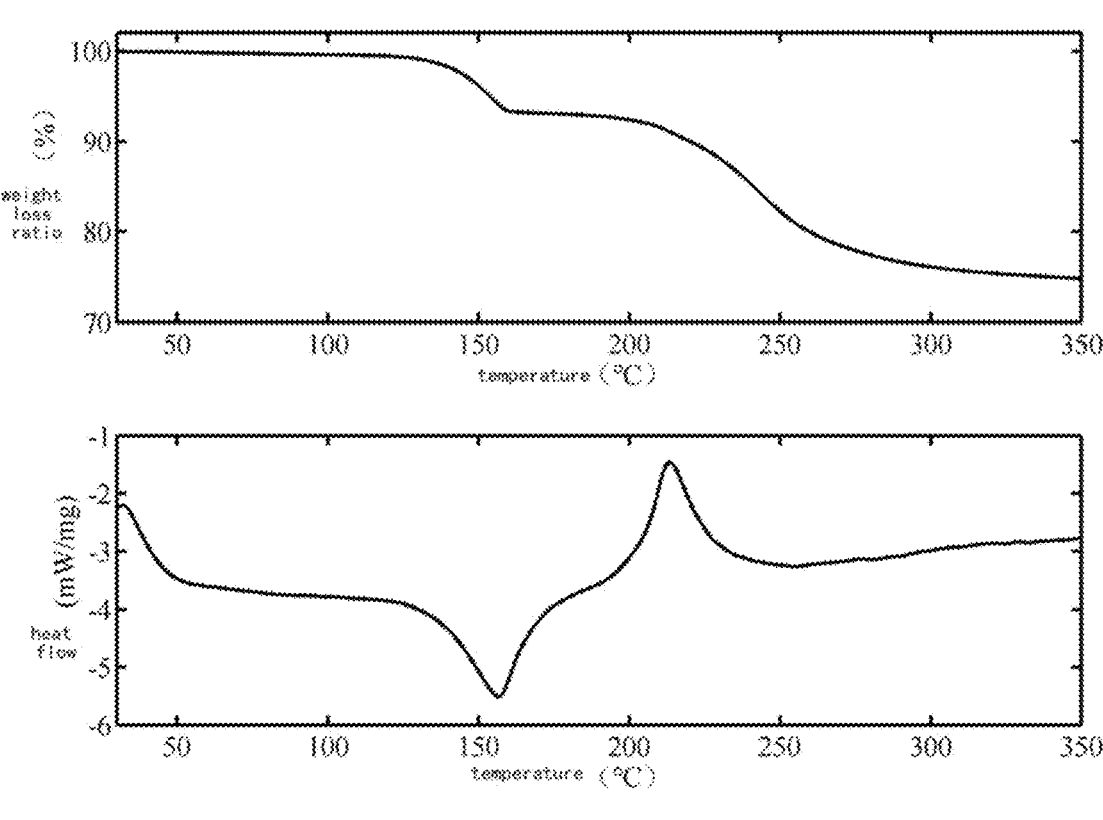
FIG. 7 shows a thermogram of esomeprazole magnesium trihydrate.
Figure 8:
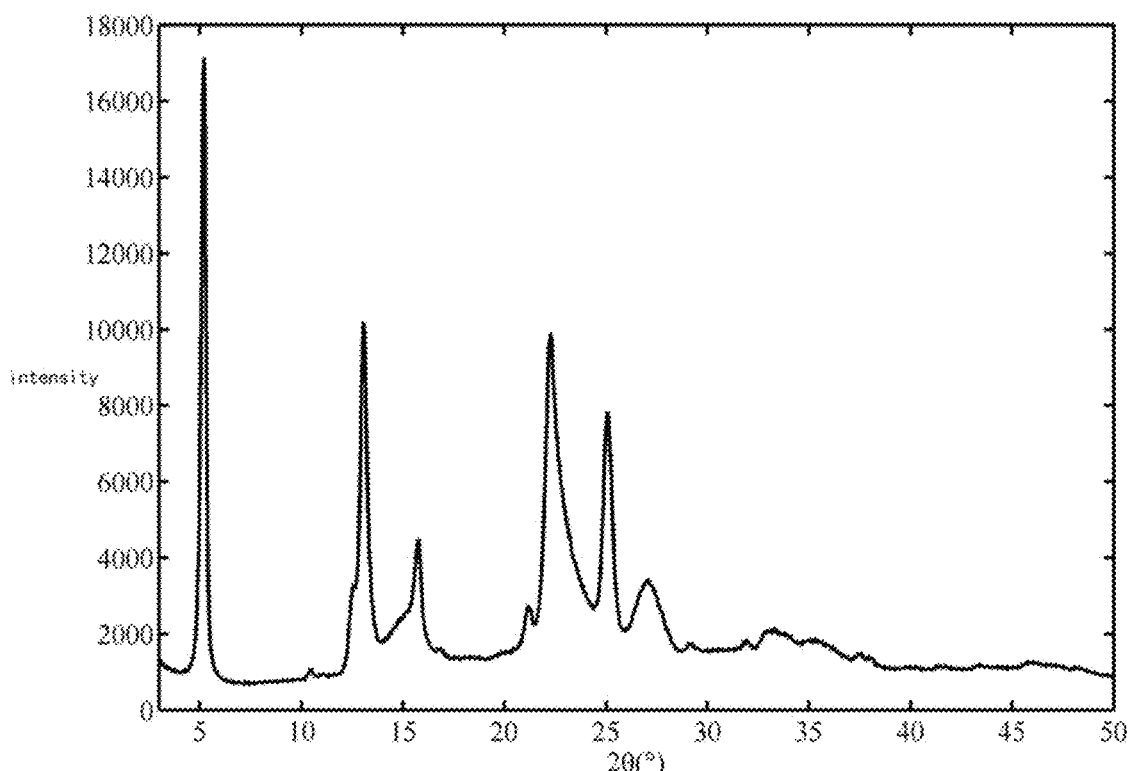
FIG. 8 shows an XRD spectrum of esomeprazole magnesium trihydrate.
Figure 9:
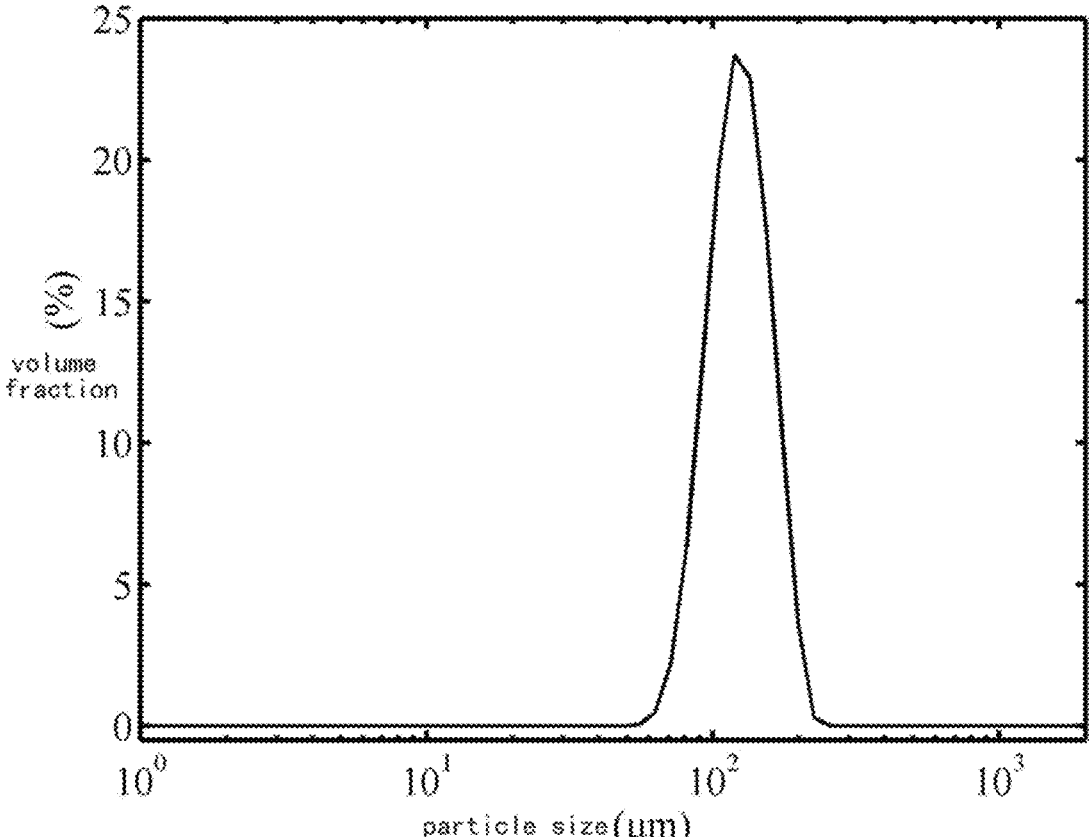
FIG. 9 shows a particle size distribution diagram of esomeprazole magnesium trihydrate obtained in Embodiment 5.

It can be seen from the comparison between FIG. 1 and FIG. 5, esomeprazole magnesium tetrahydrate and esomeprazole magnesium trihydrate are obviously different in distribution state, and esomeprazole magnesium trihydrate has good dispersion and uniform particles. It can be seen from the comparison between FIG. 2 and FIG. 6 that esomeprazole magnesium tetrahydrate is a bulk substance, while esomeprazole magnesium trihydrate is a sheet substance. It can be seen from the comparison between FIG. 3 and FIG. 7, the thermal weight loss diagram above in FIG. 3 shows that the sample has two weight loss steps before 170° C. It can be seen from the differential scanning heat map in FIG. 3 below, both weight losses are endothermic and correspond to the removal of water molecules, the total weight loss thereof is 9.4%, corresponding to 4 water molecules, so the product is esomeprazole magnesium tetrahydrate. It can be seen from the thermal weight loss diagram in FIG. 7 above, the sample has a weight loss step before 170° C. It can be seen from the differential scanning heat map in FIG. 3 below, this weight loss is endothermic, so it also corresponds to the removal of water molecules, the weight loss thereof is 6.9%, corresponding to three water molecules, so the product is esomeprazole magnesium trihydrate. It can be seen from the comparison between FIG. 4 and FIG. 8, esomeprazole magnesium tetrahydrate and esomeprazole magnesium trihydrate are obviously different in the XRD spectrum. It can be seen from FIG. 9 that the particle size of esomeprazole magnesium trihydrate obtained by the method of the present invention is relatively large, with the mean particle size of more than 100 μm.

The invention claimed is:
1. A method for preparing esomeprazole magnesium trihydrate by crystal transformation, comprising the following steps:
① preparation of esomeprazole potassium aqueous solution: according to part by weight, adding 35~45 parts of esomeprazole potassium into 500~1000 parts of the first deionized water, stirring and dissolving them, and filtering the mixture with 0.45 microns of aqueous phase filter membrane to obtain the esomeprazole potassium aqueous solution;
② preparation of magnesium sulfate heptahydrate aqueous solution: adding 15~20 parts of magnesium sulfate heptahydrate into 280~420 parts of the second deionized water, stirring and dissolving them, and filtering the mixture with 0.45 microns of aqueous phase filter membrane to obtain the magnesium sulfate heptahydrate aqueous solution;

③ reactive crystallization process: adding the esomeprazole potassium aqueous solution obtained in Step ① into a crystallization kettle, controlling the temperature of the crystallization kettle at 15~20° C., starting to stir, adding the magnesium sulfate heptahydrate aqueous solution obtained in Step ② and with the mass of 1/10~1/8 into the crystallization kettle, stirring them for 10~15 minutes, and then adding the remained magnesium sulfate heptahydrate aqueous solution obtained in Step ② into the crystallization kettle within 30 minutes, and stirring at 15-20° C. for crystallization for 30~40 minutes to obtain the esomeprazole magnesium tetrahydrate; and ④ filtering the esomeprazole magnesium tetrahydrate obtained in Step ③, washing the filter cake in the deionized water, putting the filter cake into a vacuum drier, and drying at 35~45° C. for 5~6 hours to obtain a sphaerocrystal of esomeprazole magnesium trihydrate.

2. The method for preparing esomeprazole magnesium trihydrate by crystal transformation according to claim 1, wherein Step ① is as follows: adding 40 parts of esomeprazole potassium into 600 parts of the first deionized water.

3. The method for preparing esomeprazole magnesium trihydrate by means of crystal transformation according to claim 1, wherein Step ② is as follows: adding 17 parts of magnesium sulfate heptahydrate into 300 parts of the second deionized water.

4. The method for preparing esomeprazole magnesium trihydrate by crystal transformation according to claim 1, wherein the temperature of the crystallization kettle is 18° C.

5. The method for preparing esomeprazole magnesium trihydrate by crystal transformation according to claim 1, wherein a water soluble dispersant is added into the crystallization kettle after the magnesium sulfate heptahydrate aqueous solution is added, the mass of the water soluble dispersant is 1~5% of the mass of the esomeprazole potassium in Step ①, and the water soluble dispersant is isomeric alcohol ethoxylates or sodium ligninsulfonate.

* * * * *